United States Patent

Andrew et al.

[11] Patent Number: 6,074,358
[45] Date of Patent: *Jun. 13, 2000

[54] METHOD AND APPARATUS FOR LENTICULAR LIQUEFACTION AND ASPIRATION

[76] Inventors: Mark S. Andrew; Mylina Andrew, both of 314 Avondale Ave., Haddonfield, N.J. 08033

[*] Notice: This patent is subject to a terminal disclaimer.

[21] Appl. No.: 08/823,713

[22] Filed: Mar. 25, 1997

Related U.S. Application Data

[62] Division of application No. 08/384,655, Feb. 6, 1995, Pat. No. 5,616,120.

[51] Int. Cl.[7] .................................................. A61M 1/00
[52] U.S. Cl. ............................. 604/28; 604/35; 604/43; 604/113; 606/107
[58] Field of Search .......................... 604/22, 27, 28, 604/35, 113–114, 43; 606/6, 24, 25, 107, 169, 170; 607/96, 99, 104

[56] References Cited

U.S. PATENT DOCUMENTS

| | | | |
|---|---|---|---|
| 3,247,851 | 4/1966 | Seibert | 128/254 |
| 3,351,063 | 11/1967 | Malaker et al. | 128/303.1 |
| 3,589,363 | 6/1971 | Banko | 128/276 |
| 3,693,613 | 9/1972 | Kelman | 128/24 A |
| 3,906,954 | 9/1975 | Baehr et al. | 128/305 |
| 3,994,297 | 11/1976 | Kopf | 128/276 |
| 4,019,514 | 4/1977 | Banko | 128/230 |
| 4,078,564 | 3/1978 | Spina et al. | 128/216 |
| 4,135,516 | 1/1979 | Spina et al. | 128/303 |
| 4,191,176 | 3/1980 | Spina et al. | 128/1 |
| 4,386,927 | 6/1983 | Eichenbaum | 604/51 |
| 4,411,652 | 10/1983 | Kramer et al. | 604/153 |
| 4,436,722 | 3/1984 | Matsunaga et al. | |
| 4,496,342 | 1/1985 | Banko | 604/27 |
| 4,597,388 | 7/1986 | Koziol et al. | 128/303.1 |
| 4,650,461 | 3/1987 | Woods | 604/28 |
| 4,694,828 | 9/1987 | Eichenbaum | 128/303.1 |
| 4,744,360 | 5/1988 | Bath | 128/303.1 |
| 4,764,165 | 8/1988 | Reimels et al. | 604/35 |
| 4,804,364 | 2/1989 | Dieras et al. | 604/22 |
| 4,817,599 | 4/1989 | Drews | 128/303 |
| 4,869,715 | 9/1989 | Sherburne | 604/22 |
| 4,886,491 | 12/1989 | Parisi et al. | 604/22 |
| 4,990,159 | 2/1991 | Kraff | 623/6 |
| 4,995,880 | 2/1991 | Galib | 623/6 |
| 5,022,413 | 6/1991 | Spina, Jr. et al. | 128/898 |
| 5,061,255 | 10/1991 | Grenfield et al. | 604/266 |
| 5,246,435 | 9/1993 | Bille et al. | 606/6 |
| 5,257,988 | 11/1993 | L'Esperance, Jr. | 604/22 |
| 5,322,504 | 6/1994 | Doherty et al. | 606/167 |
| 5,324,319 | 6/1994 | Mason et al. | 607/104 |
| 5,403,306 | 4/1995 | Edwards et al. | |
| 5,451,208 | 9/1995 | Goldrath | 604/55 |
| 5,496,270 | 3/1996 | Nettekoven | 604/30 |
| 5,616,120 | 4/1997 | Andrew et al. | 604/28 |

*Primary Examiner*—Mark Bockelman
*Attorney, Agent, or Firm*—Norman E. Lehrer

[57] ABSTRACT

A technique is described for liquefying, or gelifying, a hardened, cataractous lens nucleus and aspirating the same. Heat or heated solution is delivered to the lens nucleus in vivo so that the heat or heated solution is placed in contact with the hardened nucleus in order to heat and liquefy the same. The lens nucleus is irrigated simultaneously with a cooled solution to thereby limit to a very small area where the heat or heated solution is present in the eye. This allows the surgeon precise control over which intraocular anterior segment structures are exposed to the heat or heated solution. The liquefied lens nuclear material is then aspirated from the eye. The above allows the removal of a lens nucleus through a 1 to 2 mm corneal or limbal incision which is smaller than the smallest incision allowable with previously known small incision cataract techniques. The above benefits the patient as it allows small incision cataract removal to be done in a way that is non-traumatic to intraocular structures. The above benefits the surgeon, and the patient, in that it is a relatively straightforward and easy surgical maneuver for the surgeon to perform. This is in stark contrast to current phacoemulsification, which is potentially very traumatic to intraocular structures, and which is a relatively difficult surgical maneuver to perform.

9 Claims, 1 Drawing Sheet

METHOD AND APPARATUS FOR LENTICULAR LIQUEFACTION AND ASPIRATION

This is a division of prior application Ser. No. 08/384,655, filed Feb. 6, 1995, now U.S. Pat. No. 5,616,120.

BACKGROUND OF THE INVENTION

The present invention relates to cataract surgery and, more particularly, to a method and apparatus for liquefying, or gelifying, a hardened, cataractous lens and aspirating the same from an eye. This method and apparatus allows for cataract removal through a very small incision, in either the peripheral cornea or surgical limbus. The unequivocal superiority of this method and apparatus compared to present small incision cataract extraction techniques is that it is non-traumatic to intraocular structures, that it is much easier for the surgeon to perform, and that it allows for a smaller incision.

The lens of an adult human eye is about 9 millimeters in diameter and about 5 millimeters thick. A lens capsule, which is the basement membrane of the lens epithelial cells and which has structural integrity, surrounds the lens. The lens, internal to the capsule, is comprised of a nucleus and a cortex. The cortex is a soft, thin layer which surrounds the centrally located nucleus.

The nucleus is comprised of an outer nucleus and an inner nucleus. The outer nucleus is soft regardless of the age of the patient. The inner nucleus is normally soft until approximately the age of 45. After a person attains this age, however, the inner nucleus becomes progressively harder. In some instances, the inner nucleus becomes very hard. When the inner nucleus is soft and relatively elastic, the lens readily changes shape in order to focus, a process known as accommodation. As one grows older and the inner nucleus hardens, the ability of the lens to accommodate decreases. Glasses can be worn in order to correct this deficiency. Wearing glasses will not, however, correct the vision of a person who has a significant cataract.

An eye becomes cataractous when the lens becomes opaque. Cataracts cause diminished vision. If the degree of opaqueness is significant the cataractous lens may be surgically removed. For many years, the most prevalent surgical procedure for removing a cataractous lens was intracapsular extraction. In an intracapsular procedure, the entire lens along with the capsule is removed. A major drawback with this procedure is that the resulting aphakic (lensless) eye has no capsule. Therefore, because there is no capsule there is no capsular support for a posterior chamber intraocular lens (IOL).

Extracapsular lens removal has rapidly become the preferred method for cataract removal since the advent of intraocular lens implants. With this procedure, the anterior portion of the capsule is cut open so that the cataractous lens can be removed. However, the equatorial and posterior portions of the lens capsule are left intact. Once the cataractous lens nucleus and cortex are removed, the implant can be inserted therein. In traditional extracapsular cataract extraction, the lens nucleus is delivered manually. A drawback of this is that a relatively large incision (from 8 mm to 11 mm) must be made in the limbus in order to remove the cataractous lens. That large of an incision causes a relatively lengthy post-operative healing time and is often the cause of significant surgically-induced post-operative astigmatism.

In recognition of the drawbacks of the aforementioned extracapsular procedure, phacoemulsification was introduced. This technique involves the utilization of an irrigation/aspiration handpiece that has an ultrasonic tip attached to the distal end thereof. See, for example, U.S. Pat. No. 3,693,613. The ultrasonic tip, which is rather sharp and made of metal, vibrates approximately 40,000 times per second in order to break up the lens nucleus into tiny pieces so that these pieces can then be aspirated from the eye. The advantage of phacoemulsification is that it allows lens nucleus removal through a relatively small incision of about 3 mm. The disadvantage, however, is that it has proven to be relatively dangerous since the ultrasonic tip destroys any and all tissue that gets in its way. If the vibrating tip comes into contact with the cornea, iris, or capsule, it can cause serious and permanent damage. Moreover, during the break up of the hard nucleus, a chip can break off and effectuate a tear in the posterior capsule. Another disadvantage of phacoemulsification is that it requires a very high degree of skill, concentration and experience on the surgeon's part for it to be performed well on a consistent basis.

Due to the above, cataract surgeons desire a small incision cataract extraction procedure which is inherently safer and easier to perform than phacoemulsification. U.S. Pat. Nos. 4,078,564, 4,135,516, 4,191,176 and 5,022,413 suggest an alternative method for liquefying the hard nucleus so that the same can be aspirated from the eye. The patents describe a method of liquefying the cataractous lens by injecting a concentrated solution of a lens digesting enzyme onto the lens and thereafter removing the enzyme digested lens material. A drawback with this method is that it takes, at a minimum, 12 to 48 hours for the enzyme to soften the hardened nucleus material. Accordingly, the cataractous lens can not be liquified and simultaneously aspirated from the lens capsule. Furthermore, it is not believed that very hard nuclei would liquefy with this enzyme technique.

Other methods have also been proposed for breaking up the hardened nucleus so that the same can be aspirated. These methods are described, for example, in U.S. Pat. Nos. 4,744,360 and 4,597,388. To Applicant's knowledge, however, none of these methods has ever been successfully utilized.

SUMMARY OF THE INVENTION

The present invention is designed to overcome the deficiencies of the prior art discussed above. It is an object of the invention to provide a method and apparatus for safely liquefying the hardened nucleus of a lens, so as to allow its removal by aspiration. This would allow for lens nucleus removal through a very small incision of 1 to 2 mm in either peripheral cornea or surgical limbus.

In accordance with the illustrative embodiments and demonstrating features of the present invention there is provided a technique for liquefying a hardened nucleus of a cataractous lens based on the finding that the nucleus can be melted or liquified if heated to an appropriate temperature. The liquified nucleus can then be aspirated. According to the invention, a 1 to 2 mm incision is made into either the cornea or limbus and an opening is made in the anterior lens capsule. A heated solution is then delivered to the lens nucleus though the anterior capsule opening so that the solution contacts the hardened nucleus in order to liquify or gelify the same. The lens nucleus is irrigated with a cooled solution while the heated solution is being delivered to the nucleus. This simultaneous cooled solution is provided to limit to a very small area (of from about 1 to 2 mm) where the solution is actually hot. This allows the surgeon precise control over what intraocular anterior segment structures are exposed to heat or heated solution. The only exposed structures will be lens cortex, nucleus and capsule. The lens capsule, however, is not structurally damaged when exposed to the heated solution. The liquified nucleus is then aspirated and the lens cortex is removed by standard irrigation/aspiration technology.

As used in this application, the term liquefy is intended to encompass the concept of gelify or gelifaction. That is, liquefy or liquefaction implies changing a hardened lens nucleus into a liquid or into a soft enough gel-like substance so that it can be aspirated from the eye by standard aspiration devices.

Other objects, features and advantages will be readily apparent from the following detailed description of a preferred embodiment thereof taken in conjunction with the drawings.

BRIEF DESCRIPTION OF THE DRAWINGS

For the purpose of illustrating the invention, there is shown in the accompanying drawings one form which is presently preferred; it being understood that the invention is not intended to be limited to the precise arrangements and instrumentalities shown.

DETAILED DESCRIPTION OF THE PREFERRED EMBODIMENT

Figure 1:
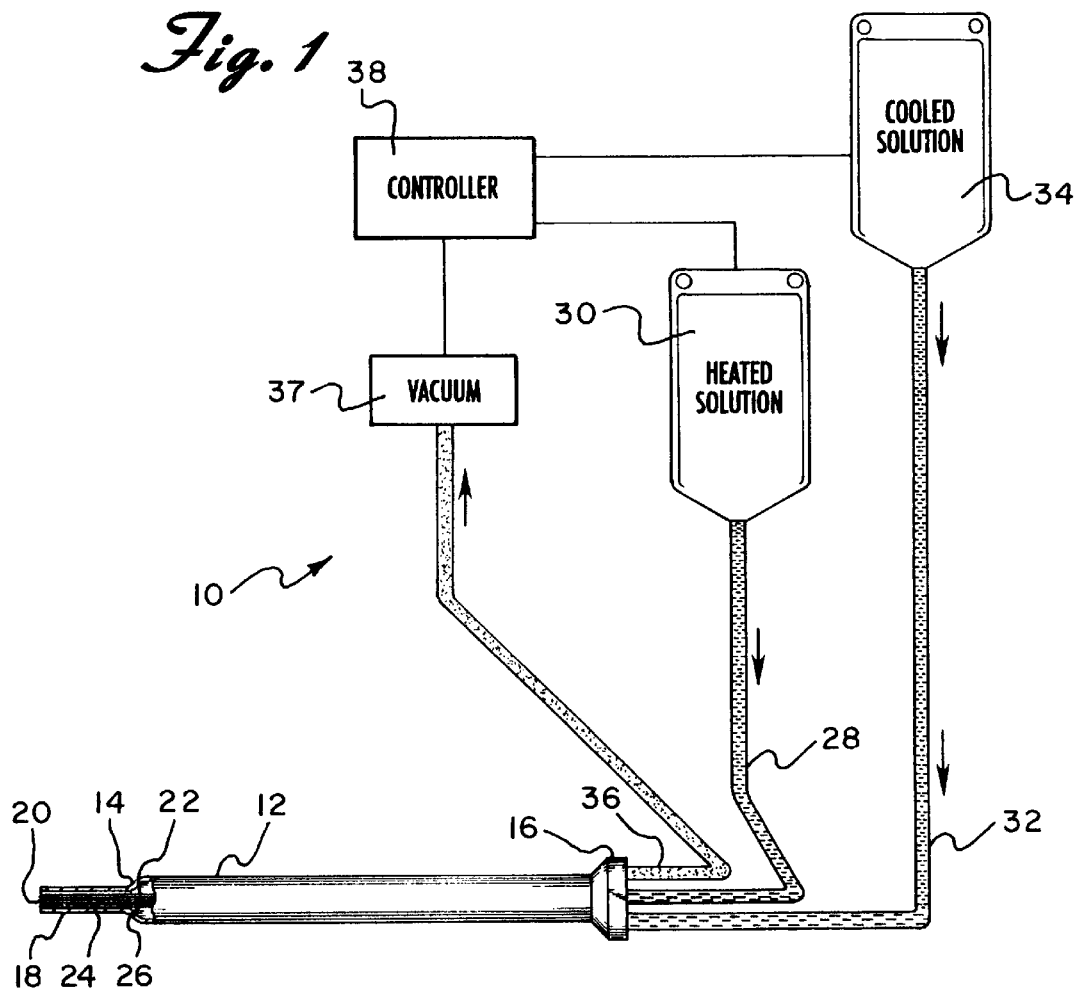
FIG. 1 is an elevational view of a lenticular liquefaction and aspiration device constructed in accordance with the principles of the present invention, and FIG. 2 diagrammatically represents a cannula inserted into the lens of a human eye.

Referring now to the drawings in detail wherein like reference numerals have been used in the two figures to designate like elements, there is shown in FIG. 1 a lenticular liquefaction and aspiration device constructed in accordance with the principles of the present invention and designated generally as 10.

The lenticular device 10 includes a hollow handpiece 12 with a first end 14 and a second end 16. An elongated cannula 18 extends from the first end 14 of the handpiece 12 and terminates in a tip 20. The tip 20 has three ports formed therethrough. Three lumens 22, 24, 26 are positioned in the cannula. Each of the lumens has one end communicating with a corresponding port and an opposite end extending into the handpiece 12.

An irrigation tube 28 has one end thereof connected to the lumen 24 and an opposite end connected to a fluid source 30. The fluid source is heated by a heating element (not shown) that can be located within or outside of the handpiece 12. The heated fluid source 30 supplies heated fluid through the heated irrigation tube 28 and out of the tip 20 of the cannula 18 via the port associated with the lumen 24. A preferred heated fluid is a balanced salt solution (BSS). However, a variety of other solutions that are compatible with the tissue being treated can be utilized. The optimum temperature for the solution is believed to be approximately 180° F. However, temperatures from about 110° to about 215° F. are also believed to liquify the hardened nucleus without damaging the surrounding capsule with the optimal range being about 160° to 200° F. The supply of heated BSS solution can be applied in bursts controlled by the surgeon in a manner well known in the art.

A cooled solution irrigation tube 32 has one end thereof connected to the lumen 26 and an opposite end connected to an irrigation supply source 34. The irrigation supply source supplies fluid through the irrigation tube 32 and out of the tip 20 of the cannula via the port associated with the lumen 26. Once again, the preferred irrigation solution is a balanced salt solution. The irrigation supply source is preferably mounted above the handpiece 12 so that gravity continuously feeds the irrigation solution through the irrigation tube 32 and out of the tip 20 of the cannula 18. This irrigation solution should preferably be chilled pre-operatively as in current phacoemulsification techniques, or may be cooled intra-operatively. The preferred temperature for the cooled solution is believed to be approximately 40° F., although the optimal temperature will vary depending on the temperature of the heated solution and the configuration of the tip 20.

An aspiration tube 36 has one end connected to the lumen 22 and the opposite end connected to a vacuum source 37. The vacuum source 37 causes the lens material and the BSS to be aspirated from the lens through the tip 20 of the cannula via the port associated with the lumen 22. The liquified lens material is disposed of by means well known in the art. It should be noted that all of the above operations are preferably controlled through a controller circuit 38.

Figure 2:
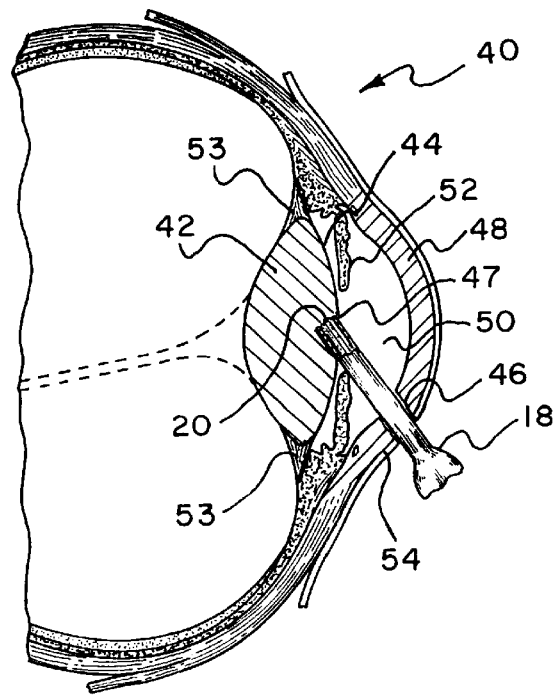

To facilitate an understanding of the principles associated with the foregoing arrangement, its operation will now be briefly described. Referring to FIG. 2, a human eye 40 is shown which includes a cataractous lens nucleus 42. As is well known, the nucleus 42 is surrounded by a cortex. The lens nucleus 42 is further encompassed by a lens capsule 44. A small incision 46 is made in the cornea 48, or in the limbus 54, to allow the tip 20 of the cannula 18 to be inserted therein. An opening 47 is made in the lens capsule. The cannula 18 is passed through anterior chamber 50 and through the opening 47 in the lens capsule 44. Accordingly, the tip 20 of the cannula is placed in contact with the cataractous lens nucleus 42.

A cooled solution, preferably BSS, is fed through the irrigation tube 32, through the lumen 26 and out the corresponding port in the tip 20 of the cannula 18. The flow from the irrigation source 34 is controlled by the surgeon in a manner well known in the art (e.g. a foot actuated flow control switch).

Heated BSS is fed through the tube 28, through the lumen 24 and out the tip 20. The only portion of the eye that contacts the tip 20 when the heated BSS is being emitted therefrom is the cataractous lens nucleus 42. Upon contact with the heated BSS, the cataractous lens rapidly liquifies. The cooled BSS from the irrigation tube 32 rapidly cools the heated BSS so that the cornea 48, the iris 52 and the zonules 53 will not be exposed to heated BSS. Accordingly, thermal damage to any of the aforementioned structures will be avoided.

The liquified lens and the BSS are aspirated through the lumen 22 and through the aspirating tube 36 when the vacuum source 37 is activated in a manner well known in the art such as through the use of a foot pedal. The aspiration and the irrigation of the lens take place simultaneously. Furthermore, it should be pointed out that the aspiration takes place substantially throughout the procedure. That is, it is believed that it is not necessary nor desirable to liquify the entire lens nucleus before aspirating the same. Rather, as a portion of the lens nucleus is liquified by the heated solution, it is irrigated by the cooled solution and aspirated. This process continues until the entire lens nucleus has been liquified and aspirated. Once the lens nucleus and cortex are evacuated from the lens capsule 44, an intraocular lens implant can be inserted through a small enlargement of the incision 46 and the opening 47 in the lens capsule 44.

EXPERIMENT 1

A cataractous lens was removed from a 56 year old patient via an extracapsular procedure. The hardened lens nucleus was placed in a specimen container. A solution of BSS was heated in a cup to approximately 180° F. The solution was drawn into a 5 cc syringe. With a 25 gauge needle, the heated solution was injected into a portion of the lens nucleus. The portion of the lens nucleus contacted by the heated BSS immediately liquified. In addition, the lens nucleus, which was originally a dark yellow, became clear upon liquefaction. The resultant liquid was clear, not yellow. The BSS was allowed to cool to a temperature under 180° F., but still hot. Injection of this cooler BSS into the lens nucleus turned it into a soft gummy gel that was light grey in color. That is, it changed from a yellow solid mass to a light grey gel. The resultant gel was of a soft enough nature that it could be aspirated from the eye with standard irrigation/aspiration technology.

EXPERIMENT 2

A cataractous lens was removed from an 80 year old patient via an extracapsular procedure. The hardened, brunescent lens nucleus was treated with a solution of BSS that was heated to approximately 180° F. The nucleus instantaneously liquified. Next, a piece of the anterior capsule was contacted with BSS solution at approximately 180° F. An inspection of the capsule under operating room microscope (Zeiss) magnification indicated no obvious structural damage to the same.

Although the present invention has been particularly described as a method and apparatus for lenticular liquefaction and aspiration for the purpose of removing a hardened lens nucleus and thereafter replacing the same with an intraocular implant, it is contemplated that the invention may have broader implications. By way of example and not limitation and as a direct result of the small capsulotomy size allowed by use of the present invention, it may be possible to develop a methodology to kill all lens epithelial cells and remove them at the time of cataract surgery, thus preventing post-operative lens capsule opacification. Furthermore, a malleable, injectable gel-like IOL, could be inserted through the 1 to 2 mm anterior capsulotomy resulting from the lenticular liquefaction and aspiration according to the invention. This would provide the patient with an almost completely intact capsule (anterior, equatorial and posterior) at the end of surgery that would not opacify after surgery, and that would be comprised of the clear, malleable gel-like IOL. The end result of that surgery would be a clear lens that accommodates. This would simulate a state very close to the natural lens prior to the onset of either cataract or presbyopia. Current cataract extraction techniques require too large of an anterior capsulotomy to allow the above to occur.

The above surgery could become a refractive surgical procedure for the treatment of presbyopia; wherein the surgery would be done to remove the lens simply because it is getting too hardened to accommodate properly, even when it is not cataractous.

As indicated above, the heated solution delivered to a yellowed, cataractous lens changed the lens color dramatically from a yellow to a clear liquid, or to a light grey gel. (A non-cataractous lens normally has a light grey hue.) As a result, the possibility exists of being able to deliver heat or heated solution to the lens to clarify it, to remove the opacity, without having to remove the lens from the eye.

The present invention may be embodied in other specific forms without departing from the spirit or essential attributes thereof and accordingly reference should be made to the appended claims rather than to the foregoing specification as indicating the scope of the invention.

What is claimed is:

1. In a method for treating cataracts in vivo by liquefying a cataractous lens nucleus and aspirating the same from within a surrounding lens capsule comprising the steps of:

delivering a heated fluid having a temperature in the range of about 110° F. to 215° F. directly into said lens nucleus in order to liquify the same without vibrating any portion of said lens nucleus;

irrigating said lens nucleus, and aspirating said liquified lens nucleus while continuing to irrigate the same.

2. The method of claim 1 wherein said fluid is comprised of a saline solution.

3. The method of claim 1 further including effectuating an opening in said lens capsule, said heated fluid being delivered into said opening and said liquified lens nucleus being aspirated out of said opening.

4. The method of claim 1 wherein said liquified lens nucleus is irrigated with a cooled solution so that said lens nucleus and said heated fluid are cooled.

5. In a method for treating a cataractous lens in vivo by liquefying a hardened nucleus of a cataractous lens and aspirating the same from a surrounding lens capsule comprising the steps of:

effectuating an opening in said lens capsule;

delivering a heated solution having a temperature in the range of about 110° F. to 215° F. through said opening so that said heated solution comes into contact with said hardened nucleus in order to liquify the same without vibrating any portion of the lens nucleus;

irrigating said lens nucleus with a cooled solution while carrying out the heated solution delivery step, and aspirating said liquified nucleus while continuing to irrigate the same.

6. The method of claim 5 wherein said heated solution is comprised of a balanced salt solution.

7. In a method for treating hardened lens nucleus in vivo by liquefying a hardened lens nucleus wherein the improvement comprises liquefying said lens nucleus by heating the same to a temperature of about 110° F. to about 215° F. without vibrating any portion of the lens nucleus.

8. The method of claim 7 wherein said lens nucleus is heated by contacting the same with a heated fluid.

9. The method of claim 8 wherein said fluid is a saline solution.

* * * * *